United States Patent [19]
Fanelli

[11] Patent Number: 5,718,908
[45] Date of Patent: Feb. 17, 1998

[54] TOPICAL FORMULATIONS BASED ON MINERAL GELS

[75] Inventor: Mauro Fanelli, Marta, Italy

[73] Assignee: Geomedical S.R.L., Milan, Italy

[21] Appl. No.: 670,168

[22] Filed: Jun. 27, 1996

[30] Foreign Application Priority Data

Aug. 14, 1995 [EP] European Pat. Off. ............ 95112772

[51] Int. Cl.$^6$ .................................................. A61K 7/48
[52] U.S. Cl. .................................... 424/401; 514/887
[58] Field of Search .......................... 424/401, 78.03; 514/887

[56] References Cited

FOREIGN PATENT DOCUMENTS

37715A2850228  2/1986  Hungary.
58-159406      9/1983  Japan.

OTHER PUBLICATIONS

Pct International Application, WO 9308793 A1 Kemp Colyn Roy; Robertson, Mandy Dawn Leyland, Robert Leslie Boots Co. PLC uk, May 13, 1993.

*Primary Examiner*—Thurman K. Page
*Assistant Examiner*—D. Faulkner
*Attorney, Agent, or Firm*—Griffin, Butler, Whisenhunt & Kurtossy

[57] ABSTRACT

The present invention relates to topical formulations containing a gel or suspension obtainable by treatment of suitable pulverized minerals with aqueous solutions. The compositions of the invention can be used for the topical treatment of degenerative diseases of cartilage, and of skin damage due to ageing or exposure to electromagnetic radiation, associated with free radicals. The compositions of the invention find application in dermatology, physiotherapy and for cosmetic skin treatments.

4 Claims, No Drawings

TOPICAL FORMULATIONS BASED ON MINERAL GELS

This application is a continuation of PCT EPO 95112222.9 patented on Aug. 14, 1995.

The present invention relates to topical formulations containing a gel or suspension obtainable by treatment of suitable pulverized minerals with aqueous solutions.

The compositions of the invention can be used for the topical treatment of degenerative diseases of cartilage, and of skin damage due to ageing or to exposure to electromagnetic radiation, associated with free radicals. The compositions of the invention find application in dermatology, physiotherapy and for cosmetic treatments of the skin.

The pathogenic role of free radicals is known and has been the subject of numerous studies. In particular, the role of free radicals in chronological ageing of the skin and on its consequences, both functional and aesthetic, has been demonstrated experimentally by many authors (N. S. Ranadive—Pathol. Immunopathol. Res.—5, 118, 1986; H. S. Black—Photochem. Photobiol.—46, 213, 1987; Y. Miyachi—in "The Biological Roles of Reactive Oxygen Species in Skin"—O. Hayashi et al. Eds.—Tokyo University Press, 1987, p. 37–41; D. Darr in "Cutaneous Aging"—A. Kligman et al. Eds.—Tokyo University Press, 1988, 415–433).

It has therefore been proposed to use substances with antiradical, or more generally antioxidant, activity for the treatment of diseases or conditions in which the damaging effect of free radicals constitutes a fundamental aetiological component. Examples of substances with antiradical activity, currently in use or under investigation, include vitamin A, vitamin E, vitamin C, superoxide dismutase (SOD), polyphenolic substances such as flavonoids and flavanolignans, and derivatives of salicylic acid.

However, the antiradical activity of the products used is connected with direct contact between them and the radicals themselves, which presupposes their absorption into the circulation or into the tissues. From this standpoint, some of the aforementioned active principles (for example SOD) possess little if any capacity for cutaneous absorption; others have reduced stability (for example tocopherols and vitamin C); still others, such as β-carotene or ubidecarenone, have colorations that limit their use in formulations of the cosmetic treatment type. Moreover, in general these active principles possess other pharmacological activities in addition to antiradical activity, and can induce systemic or local toxic effects in plasma and/or tissue levels that can vary, but are attainable after topical administration. Their use therefore presents a certain degree of risk especially in cosmetic use and can induce side effects other than the therapeutic effect.

Furthermore, the use of clays as hydrating agents and absorbents, and as ion exchangers and absorbents, is known in the cosmetics sector and in other application sectors. In these cases, use is made of the structural and crystallographic characteristics of these products, which permit the interchange and trapping, between the solid phase and the dispersing medium or solvent, of cations, of substances with varying degree of solubility in water (such as fats or proteins), and of water itself.

It has now been found that minerals different from the clays in their nature, if treated appropriately can constitute the active principle of topical formulations with antiradical activity.

In particular, the invention provides topical formulations containing a gel or a suspension obtainable by treating, with aqueous solutions, a mixture of pulverized minerals from diagenetic rocks of volcanic origin consisting of:

a) one or more of the minerals selected from orthoclase, sanidine, alunite, alumina, pyroxene, marcasite, pyrite, quartz, metallic or colloidal sulphur, jarosite, limonite, biotite, omphacite, augite, halloysite, fluorite, titanite, oxides and hydroxides of the WAD type, albite, leucite, anorthite;

b) tuff or zeolite (phillipsite, analcime, chabazite);

c) one or more of the minerals selected from montmorillonite, kaolinite, bentonite, smectite.

The formulations of the invention are capable of exerting a therapeutic or preventive action by reducing the biologically damaging oxidizing radical species and can therefore be used for the treatment of degenerative diseases of cartilage; in functional and/or morphologic changes of the skin exposed to electromagnetic rays and/or chronologically aged; in inflamed areas of the dermis and in areas characterized by reduced capillary circulation. In the cosmetics sector, the compositions of the invention can be used for toning, firming, astringent, slimming, anti-acne, anti-wrinkle, anti-cellulite and anti-ageing treatments.

The compositions of the invention can be in the form of suspension or gel, which will preferably contain biologically inert excipients such as amorphous or microcrystalline silica, micronized talc, kieselguhr or suitable thickeners.

The formulations of the invention are prepared by forming suspensions of the pulverized minerals in aqueous media with a pH between 2 and 7 and preferably from waters of volcano-thermal origin or from mineral waters classified as alkaline-earth sulphate, ferruginous sulphate or carbonic-acid, with organic or inorganic salts or acids added if required. The minerals, suitably selected or inspected, are dried in an air stream at temperature not exceeding 35° C. to a content of water of crystallization $\leq 10\%$, they are ground without thermal stress and are then screened to a constant and uniform grain size of about 200 mesh/cm$^2$. The suspension of the minerals in the aqueous medium is maintained at a temperature between room temperature and 80° C., for a period of time varying from 1 to 10 hours, preferably under an inert atmosphere, for example nitrogen. During this period the suspension is stirred continuously; at the end, talc or other thickeners or excipients can be added to the suspension and it can be distributed in suitable forms for dosage. Heat-sealed aluminium envelopes are particularly preferred. The weight ratio of pulverized minerals to aqueous medium is between about 3:1 and 1:3 and is preferably equal to about 1:1.

The unit doses will preferably contain from about 1 to about 1000 g of gel.

The minerals that can be used in accordance with the present invention can be used in pure form or it is possible to use rocks that contain them to a significant extent. Rocks of volcanic origin are particularly suitable for this purpose.

The following example provides further illustration of the invention.

EXAMPLE

A 50 kg mixture consisting of equal parts by weight of orthoclase, sanidine, alunite, alumina and halloysite 7A pulverized in a mill with screens with 200 mesh/cm$^2$ is suspended in 109 liters of alkaline-earth sulphate water at pH 7. The suspension is stirred for 15 minutes every half-hour at a temperature of 75° C. for 4 hours. Then a 50 kg mixture consisting of equal parts, again by weight, of halloysite 7A and 15A, amorphous silica and quartz, ground as above, is added and stirring continues for a further 4 hours, as specified above. After addition of 20 kg of pulverized zeolite, the suspension is left to rest for 12 hours and then it is filtered with a vibrating screen with 200 mesh/cm². 80 liters of alkaline-earth sulphate water are added to the filtrate at room temperature. This is stirred for one hour, and 120 kg of powdered kaolinite are added.

After a further 12 hours the mixture is centrifuged for two hours and then filtered through a screen with 200 mesh/cm². 8 kg of talc and 8 kg of kieselguhr are added, it is centrifuged and cooled to about 30° C., and the thickened suspension is packaged under vacuum, in unit doses containing 250 g of suspension.

When it is desired to prepare a gel, the suspension obtained as above is thickened by adding Carbopol® at 1%. It is centrifuged, left to rest for 14 hours and then packaged under nitrogen in polyethylene bottles.

I claim:

1. Topical formulations containing a gel or suspension obtainable by treating, with aqueous solutions, a mixture of pulverized minerals from diagenetic rocks of volcanic origin consisting of:

a) one or more of the minerals selected from orthoclase, sanidine, alunite, alumina, pyroxene, marcasite, pyrite, quartz, metallic or colloidal sulphur, jarosite, limonite, biotite, omphacite, augite, halloysite, fluorite, titanite, oxides and hydroxides of the WAD type, albite, leucite and anorthite;

b) tuff or zeolite (phillipsite, analcime, chabazite); and c) one or more of the minerals selected from montmorillonite, kaolinite, bentonite, smectite, said aqueous solutions having a pH between 2 and 7 and being obtained from waters of volcano-thermal origin or from alkaline-earth sulphate, ferruginous sulphate or carbonic-acid mineral waters, with or without organic or inorganic salts or acids added.

2. Formulations according to claim 1, further containing inert excipients selected from amorphous or microcrystalline silica, micronized talc, and kieselguhr.

3. Formulations according to claim 1 in the form of a suspension.

4. Formulations according to claim 1 in the form of a gel.

* * * * *